Oct. 11, 1938. M. E. RANDIG Plant Pat. 294
WATER LILY
Filed July 14, 1937
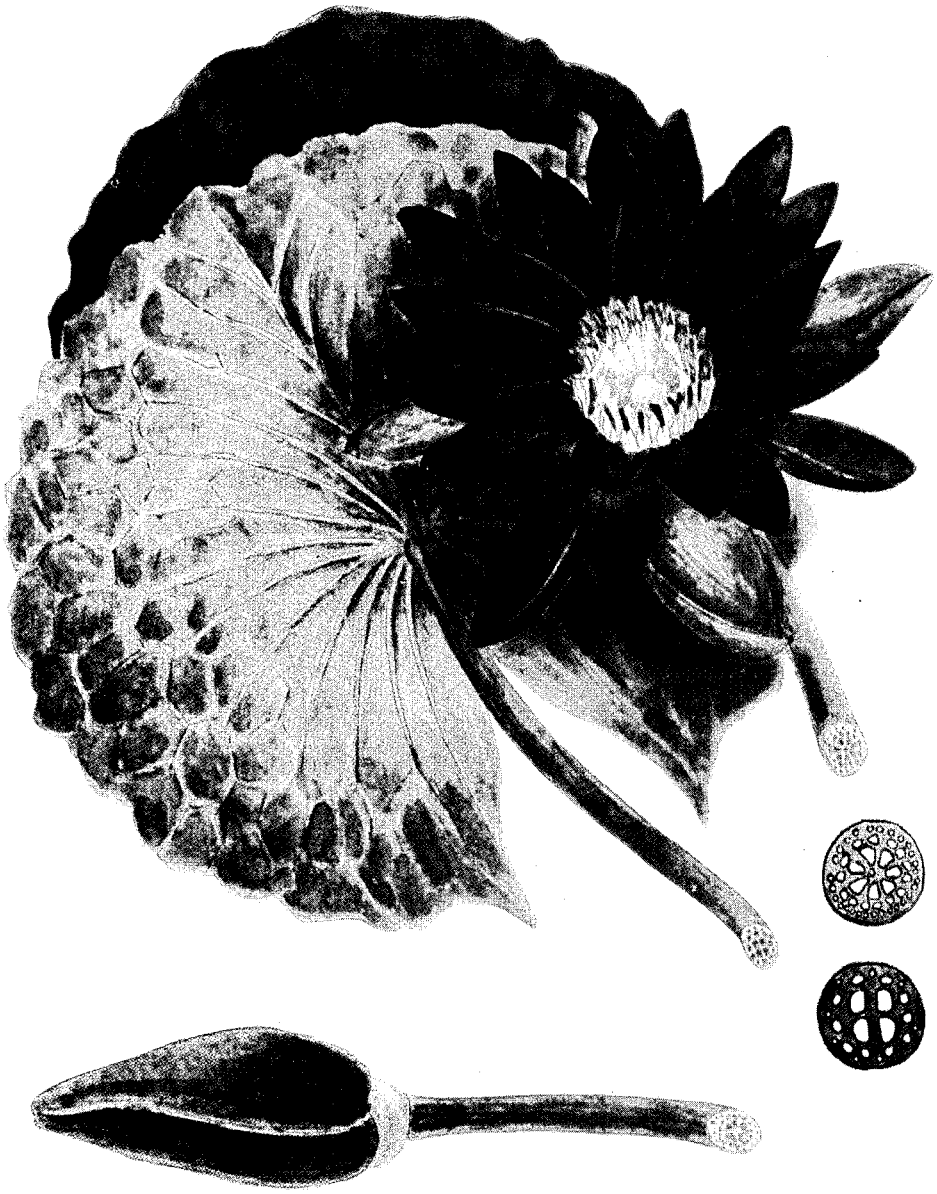
Witness:-
Tadson T. Avery
Inventor
Martin E. Randig
by: Rummler Rummler & Woodworth,
his Atty's.

Patented Oct. 11, 1938

Plant Pat. 294

UNITED STATES PATENT OFFICE

294

WATER LILY

Martin E. Randig, San Bernardino, Calif.

Application July 14, 1937, Serial No. 153,605

1 Claim. (Cl. 47—60)

The new hybrid variety of Tropical Day-blooming Nymphaea herein described was developed during a definitely planned and extensive breeding period from a parentage as follows:

N. Panama Pacific × N. Dauben } N. Lilac Queen × N. Royal Zanzibar } N. Indigo Zanzibar × N. Amethyst } the improved lily.

The improved blossoms herein illustrated were first produced in 1931 and have since been asexually reproduced by bulbs. They were first made known to the public in my February catalog of 1936.

The purposes in breeding this lily were to obtain a distinctive show flower and imperial purple petaled propagating lily; one that would have large blossoms; long-bloom period, be more hardy and have beautiful distinctive dark green leaves. This lily, which is also viviparous, is an improvement on the Panama Pacific which is a purple of the Viviparous Group. In the San Bernardino vicinity of California this lily blooms from 4 to 6 weeks earlier than the Panama Pacific. It has larger and more brilliantly colored blossoms which open at six in the morning and close at eight in the evening. The center of the blossom is a rich golden yellow instead of the average light yellow coloring.

The older leaves of this lily have an intense, polo green top color and are a distinctive maroon on the under side. The younger leaves have a satiny, olive green coloring fusing into polo green and the submerged leaves are a glistening olive green. The leaf and flower stems are a glistening cedarbark.

The accompanying illustrations show the approximately true natural colors of the lily but it must be understood that its chief characteristic, which makes it stand out among other blue lilies, is the brilliant imperial purple shading into damson blue coloring of the blossom with the golden yellow center.

In the picture the principal view shows an open blossom and the underside of a leaf. Back of this may be seen the upper side of another leaf. Below in the drawing is shown a picture of a bud and to the right in the drawing are sections of a peduncle and a petiole.

The following is a detailed description of this new variety of day-blooming lily:

*Leaves*

Submerged leaves of seedlings:
*Shape.*—Triangular.
*Color.*—Upper side—Olive Green, 15–L–4. Under side—Maroon 7–L–7.
¾ inch from petiole to sinus.

Main floating leaves:
*Shape.*—Round with serrated edges.
Submerged floating leaves turn up slightly at edges.
*Color.*—Polo Green, Upper side. Under side—Maroon.
Primary floating leaves 1 inch from petiole to sinus.

Mature leaves:
*Shape.*—Orbicular—marmorated.
*Size.*—14 to 18 inches in diameter in peak of season.
*Color.*—Upper side—Polo Green. Under side—Maroon.

Leaf stem:
*Color.*—Cedarbark 6–I–10.
*Length.*— 6 to 8 feet.

*Flowers*

*Color.*—Imperial Purple 45–G–10 shading to Damson 45–J–11.
*Size.*— 6 to 9 inches in diameter.
*Open.*—4 to 5 days.
*Fragrant.*—Very.
*Number opening at one time.*—Usually two.
Stand 6 to 9 inches out of water.

*Buds*

*Shape.*—Oviate.
*Color.*—Olive Green, 15–L–4.

*Scape*

*Color.*—Cedarbark, 6–I–10.
*Height above water.*—6 to 8 inches.
Deeply ridged longitudinally to base of ovary.

*Sepals*

*Number.*—4.
*Color.*—Olive Green on outer side. Burgundy Violet, 42–J–8 on inner side shading into Cobalt Violet, 42–J–7.
*Length.*—5½ inches.
*Width.*—1¾ inches.
*Shape.*—Ovate-triangular.
*Texture.*—Thick and fleshy.

*Petals*

*Number.*—28 to 38. In 4 whorls.
*Shape.*—Lanceolate with rounded tips.
*Length.*—4 inches.
*Width.*—1 inch.
*Color.*—Outer surface—Imperial Purple. Inner surface—Imperial Purple.
Inner whorls are staggered to outer whorls.

*Stamens*

*Number.*—175 to 180.
Outermost whorl 2½ inches long, with appendages ovate-oblong at base; linear above; Blue 43–E–10 at apex, base Golden Yellow, 10–L–7. Back of stamens Damson, front Golden Yellow divided by a Damson line down the center of each stamen.
Inner whorls shorter and narrower.
They stand erect around the stigma first day, closing over the stigma second and third days, turning out and exposing stigma fourth and fifth days.

*Carpels*

*Number.*—23.
*Color.*—Golden Yellow.
*Length.*—⅜ to ½ inch.
They curve in sharply at points, over stigma.

*Stigma*

*Color.*—Golden Yellow.
They are filled with liquid first day, dry all following days.
*Receptive.*—First day.

*Fruit*

*Shape.*—Globose.
*Size.*—2 inches in diameter.
*Seeds.*—Few.
*Fertile.*—Slightly.

The colors of this improved lily when compared with Maerz & Paul's Color Chart are as follows:

| | Section of plant | Color | Plate | Letter | Number |
|---|---|---|---|---|---|
| Blossoms | Main body petal color | Imperial Purple | 45 | G | 10 |
| | | shading into blue as | 45 | F | 10 |
| | Shading to darker edges | Damson | 45 | J | 11 |
| Sepals | Inside sepals | Cobalt Violet | 42 | J | 7 |
| | Darker section inside sepals | Burgundy Violet | 42 | J | 8 |
| | | shading into | 42 | J | 9 |
| | Edge of color on back of sepals | | 43 | L | 7 |
| | Body of back of sepals | Olive Green | 15 | L | 4 |
| Stamens | Inside tip of stamens | | 43 | E | 10 |
| | Base of stamens (yellow) | Ta-Ming | 10 | L | 6 |
| | Back of tips of stamens | Damson | 45 | J | 11 |
| Carpels | Carpels (lightest shade) | Golden Yellow | 10 | L | 7 |
| | Carpels (darkest shade) | Sunburst | 10 | K | 9 |
| Leaf | Main leaf body color | Polo Green | 23 | J | 9 |
| | Sections on edge in spots | Laurel Green | 22 | L | 1 |
| | Under area near base of stem and ribs or veins | Burnt+Yellowstone | 12 | K | 6 |
| | Underside of leaf: | | | | |
| | First or inner section | Cacao Brown | 5 | B | 11 |
| | Second section | Cedarbark | 6 | I | 10 |
| | Third or outer section | Maroon | 7 | L | 7 |
| Bud | Tip or lightest shade of bud | Palmleaf | 14 | L | 1 |
| | Body of bud | Olive Green | 15 | L | 4 |
| | Darkest section of bud at base | Argus Brown | 7 | A | 12 |
| | Ring at base of bud | Deep Stone | 13 | L | 7 |
| Stems | Leaf stem | Cedarbark | 6 | I | 10 |
| | | Maroon | 7 | L | 7 |
| | Bud and flower stem | Argus Brown | 7 | A | 12 |
| | Cross section of stems | Sponge | 14 | C | 5 |

The novel, brilliant color combination of the flower, together with its early blooming habit, good shipping and superior keeping qualities, combine to provide a very desirable and distinctly new commercial product.

I claim:

The new variety of hybrid tropical day-blooming water lily herein shown and described, having the distinctive brilliant imperial purple color of the corolla, rich golden yellow center, and the Burgundy violet color of the sepals showing between the petals, long open period, and ancestry specified.

MARTIN E. RANDIG.